(12) United States Patent
Yoneyama et al.

(10) Patent No.: US 10,048,215 B2
(45) Date of Patent: Aug. 14, 2018

(54) X-RAY IMAGING APPARATUS AND X-RAY IMAGING METHOD

(71) Applicant: Hitachi, Ltd., Tokyo (JP)

(72) Inventors: Akio Yoneyama, Tokyo (JP); Rika Baba, Tokyo (JP); Keisuke Yamakawa, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 202 days.

(21) Appl. No.: 15/114,091

(22) PCT Filed: Feb. 26, 2014

(86) PCT No.: PCT/JP2014/054708
§ 371 (c)(1),
(2) Date: Jul. 26, 2016

(87) PCT Pub. No.: WO2015/128969
PCT Pub. Date: Sep. 3, 2015

(65) Prior Publication Data
US 2017/0003233 A1    Jan. 5, 2017

(51) Int. Cl.
*G01N 23/04* (2018.01)
*G01N 23/20* (2018.01)
*G01N 23/046* (2018.01)

(52) U.S. Cl.
CPC ........... *G01N 23/046* (2013.01); *G01N 23/04* (2013.01); *G01N 23/20* (2013.01);
(Continued)

(58) Field of Classification Search
CPC ...... G01N 23/04; G01N 23/046; G01N 23/20; G01N 2223/056; G01N 2223/3306; G01N 2223/419; G01N 2223/423
See application file for complete search history.

(56) References Cited

U.S. PATENT DOCUMENTS 9,339,252 B2 *   5/2016   Sugihara ............... A61B 6/032
9,642,588 B2 *   5/2017   Goto .................... A61B 6/542
(Continued)

FOREIGN PATENT DOCUMENTS

JP    06-237927 A    8/1994
JP    11-051881 A    2/1999

OTHER PUBLICATIONS

International Search Report of PCT/JP2014/054708 dated Apr. 22, 2014.

*Primary Examiner* — Mark R Gaworecki
(74) *Attorney, Agent, or Firm* — Mattingly & Malur, PC

(57) ABSTRACT

An object of the present invention is to non-destructively obtain, in an X-ray imaging apparatus, a sectional image of a subject with spatial resolution higher than spatial resolution of an image detector. In the present invention, the image detector is two-dimensionally moved with respect to an incident X-ray for each half (180°) rotation of the subject, and a plurality of image groups (CT data sets) is obtained at different positions of the image detector. An image (sinogram) is synthesized from each image group thus obtained, which image is equal to an image obtained with a detector whose pixel size is smaller than the pixel size constituting the above described image detector. From this synthesized image, a sectional image with high spatial resolution is calculated by reconstruction calculation.

20 Claims, 14 Drawing Sheets

(52) U.S. Cl.
CPC ............... *G01N 2223/056* (2013.01); *G01N 2223/3306* (2013.01); *G01N 2223/419* (2013.01); *G01N 2223/423* (2013.01)

(56) References Cited

U.S. PATENT DOCUMENTS

| | | | |
|---|---|---|---|
| 2012/0140883 A1* | 6/2012 | Iwakiri ................ | A61B 6/4233 378/62 |
| 2012/0153177 A1* | 6/2012 | Iwakiri ................ | A61B 6/4291 250/370.09 |
| 2012/0163554 A1* | 6/2012 | Tada .................... | A61B 6/4035 378/154 |
| 2013/0235973 A1* | 9/2013 | Murakoshi ........... | A61B 6/4233 378/37 |
| 2014/0126690 A1* | 5/2014 | Yamaguchi ............ | A61B 6/484 378/36 |

* cited by examiner

X-RAY IMAGING APPARATUS AND X-RAY IMAGING METHOD

TECHNICAL FIELD

The present invention relates to an X-ray imaging apparatus and an X-ray imaging method, and particularly to an X-ray imaging apparatus and an X-ray imaging method suitable for examining inside an object non-destructively and with high spatial resolution.

BACKGROUND ART

X-ray computed tomography (CT) is a method which includes: rotating a subject relative to an X-ray source to take transmission images of the subject at different angles; and performing calculation called reconstruction using the obtained transmission images, thereby obtaining a sectional image of the subject. X-ray CT is an essential technique for medical diagnosis, since it is possible to observe inside a subject non-destructively and three-dimensionally by using high penetration of X-ray.

Spatial resolution of X-ray CT mainly depends on spatial resolution of an image detector which obtains a transmission image, and a distance (working distance (WD)) between a subject and the detector. Since there are mechanical limitations, it is generally difficult to extremely shorten the WD. Therefore, it is necessary to improve resolution of the detector in order to improve the spatial resolution.

CITATION LIST

Patent Literature

PTL 1: JP 11-051881 A
PTL 2: JP 6-237927 A

SUMMARY OF INVENTION

Technical Problem

In general, recent X-ray image detectors are roughly classified into the following two types: a direct detection type which performs direct exposure, as illustrated in FIG. 1(a), and an indirect detection type as illustrated in FIGS. 1(b) and 1(c). Examples of the direct detection-type detectors include a flat panel and a back-illuminated CCD. These detectors directly detect electron charge generated by an X-ray incident as a signal. Therefore, the spatial resolution of the detector is determined by the size of the pixel size. Since the pixel size is limited to several microns because of limitations in production processes, it has been difficult to further improve the spatial resolution.

On the other hand, the indirect detection-type detectors consist of a phosphor, a relay optical system, and an imaging device of visible light. An incident X-ray is converted to visible light by a phosphor plate, and then forms an image on a CCD or a CMOS, by a relay lens or an optical fiber. Pixel size thereof is not so different from that of the direct detection-type detector, and is about several micrometers at a minimum. Accordingly, it is necessary to increase a magnification of a lens in order to improve the spatial resolution. However, in such a case, there cause some problems such as limitation field of view, and a decrease in a light condensing efficiency, which requires a longer exposure time.

In order to solve the above-described problems, a method is proposed in which an image detector is two-dimensionally moved minutely with respect to an X-ray to obtain images, and an image with high resolution is obtained through calculation using the obtained images (see, PTL 1). However, there is the following problem: when the method is applied as it is to CT, it is necessary to move a detector minutely for each projection angle, and therefore, a circular artifact is generated when the positioning accuracy is not sufficient. In addition, there is another problem: it takes long time to move the detector, which extends the measurement time. In PTL 2, a method is proposed in which spatial resolution is improved by providing a grid to an entire surface of a detector, and moving the grid. However, in the method, there is another problem: half the intensity of X-rays is lost, which causes in an increase in radiation exposure. In addition, a method has been developed in which spatial resolution is improved by shifting a position of a detector by only ¼ of a pixel size for each half rotation in a CT measurement (quarter offset). In this case, however, the spatial resolution is improved only in a sectional direction, and the spatial resolution cannot be improved in a rotation axis direction.

Accordingly, an object of the present invention is to non-destructively obtain a sectional image of a subject with spatial resolution higher than spatial resolution of an image detector.

Solution to Problem

In order to solve the above problem, in the present invention, an image detector is two-dimensionally moved with respect to an incident X-ray for each half (180°) rotation of a subject, and a plurality of image groups (CT data sets) is obtained at different positions of the image detector. Then, an image (sinogram: an image in which a horizontal axis represents a sectional direction, and a vertical axis represents a projection angle) is synthesized from each image group, which image is equal to an image obtained with a detector whose pixel size is smaller than the pixel size of the above-described image detector. From this synthesized image, a sectional image with high spatial resolution is calculated by reconstruction calculation.

FIG. 2(a) illustrates a flowchart of procedure in a case where the concept of PTL 1 is applied to CT. In other words, the conventional flow chart of procedure indicates a method in which scanning is performed with a detector for each projection angle to obtain an image. FIG. 2(b) illustrates a flow chart of procedure according to the present invention. In the flow chart of procedure according to the present invention, a position of a detector is shifted for each half (180°) rotation of a specimen, and thereby the number of times of movement of the detector can be significantly reduced, and measurement time can be shortened.

In addition, with the flow chart of procedure according to the present invention, a positional error occurring when moving a detector is eliminated as illustrated in FIG. 3(b) (described later in detail), and a circular artifact caused by the positioning error can be suppressed. For reconstruction processing of a synthesized image, reconstruction calculation using filtered back projection, iterative reconstruction, or the like, can be used as is the case in a conventional method.

Advantageous Effects of Invention

According to the present invention, it is possible to non-destructively obtain a sectional image of a subject with spatial resolution higher than spatial resolution of an image detector.

DESCRIPTION OF EMBODIMENTS

Figure 1:
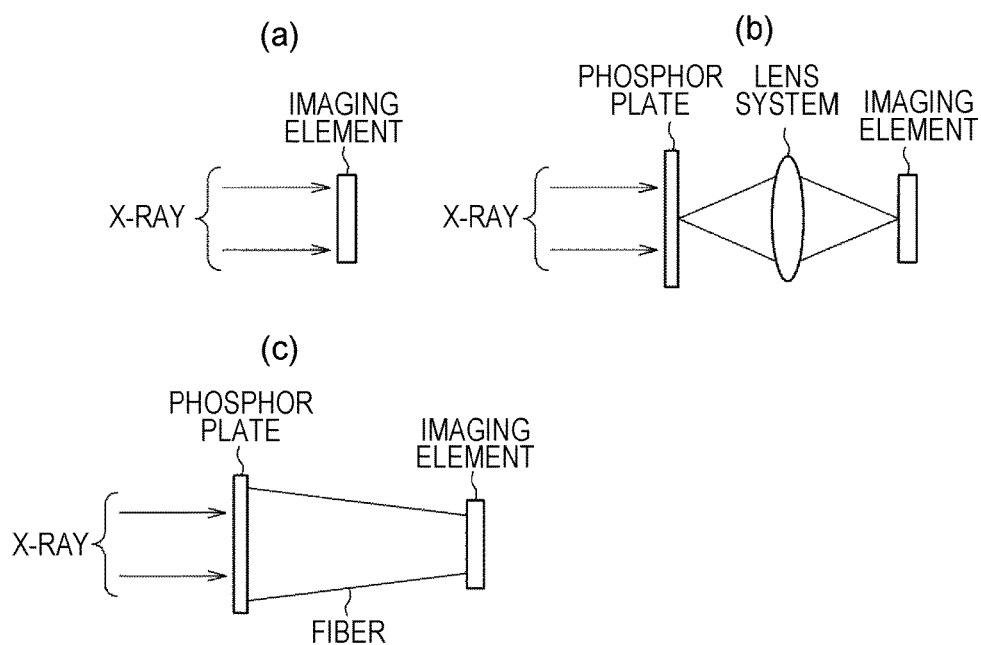
FIGS. 1(a) to 1(c) are diagrams illustrating major types of image detectors and configurations thereof.

Hereinbelow, embodiments of the present invention will be described using the drawings. In the drawings indicated blow, units having the same function are denoted by the same sign, and a repetitive description will be omitted.

Figure 2:
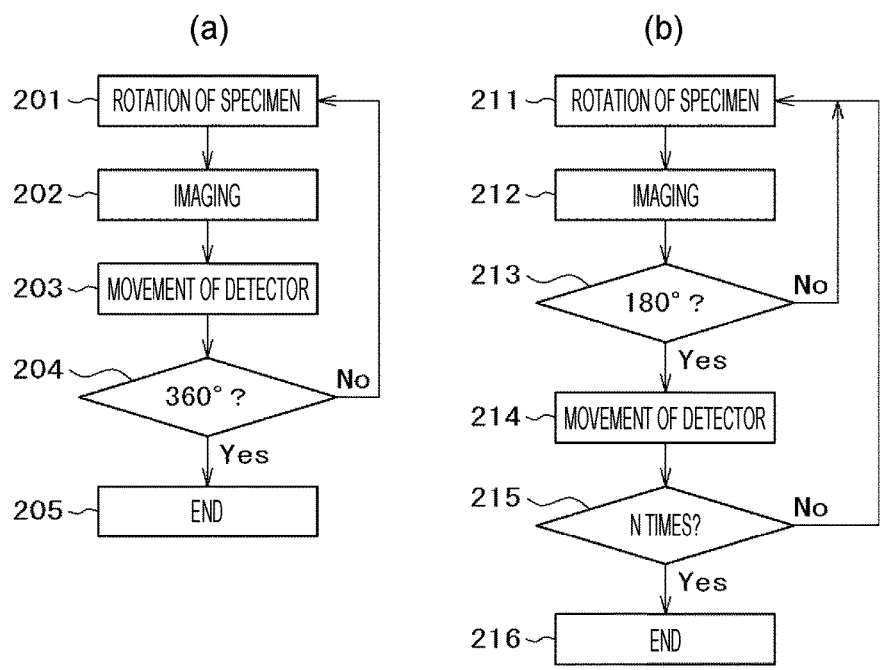
FIGS. 2(a) and 2(b) are charts illustrating a flow of procedure according to (a) a continuation of conventional inventions, and (b) the present invention.
Figure 3:
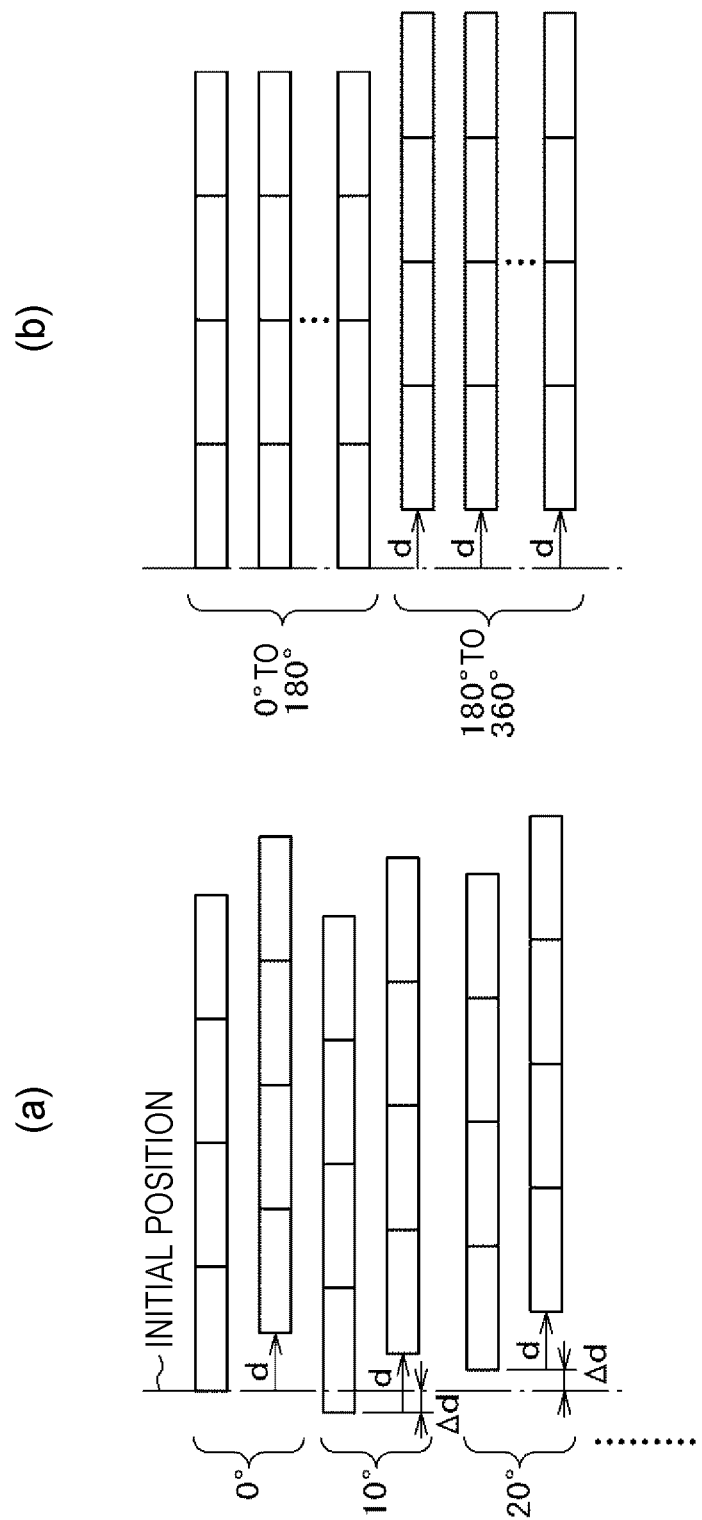
FIGS. 3(a) and 3(b) are diagrams illustrating advantageous effects of the present invention.

FIG. 3(a) illustrates a conventional case illustrated in FIG. 2(a). Projection angles (0°, 10°, 20°, . . . ) are illustrated in a vertical direction, and one row of detectors, which include a plurality of pixels, is schematically illustrated in a horizontal direction. The following case is exemplified: at a projection angle (0°), a left end portion of the detector is disposed on an initial position, and subsequently, is moved toward right by only a moving distance d. Next, at a projection angle (10°), the moved detector is returned to the initial position, but a shift from the initial position (in the drawing, toward left) is caused by a return error. In the next movement of the detector, the detector is moved from the shifted position by only the moving distance d. In the manner described above, the detector is moved for each projection angle to obtain images. Therefore, it is likely that a positioning shift error occurs whenever the projection angle is changed.

FIG. 3(b) illustrates a case according to the present invention illustrated in FIG. 2(b). Projection angles (0° to 180° and 180° to 360°) are illustrated in a vertical direction, and one row of detectors, which include a plurality of pixels, is schematically illustrated in a horizontal direction. The following case is exemplified: the detector remains disposed at the initial position and is not moved until the projection angle has been changed from 0° to 180° in increments of a constant angle, and has reached 180°. When the projection angle is then changed from 180° to 360°, the detector is moved toward right only once by only the moving distance d. When the projection angle is 0° to 180°, the detector is not moved. Therefore, the positioning error is not generated. In addition, when the projection angle is 180° to 360°, the detector is not moved. Therefore, the positioning error is not generated.

Figure 4:
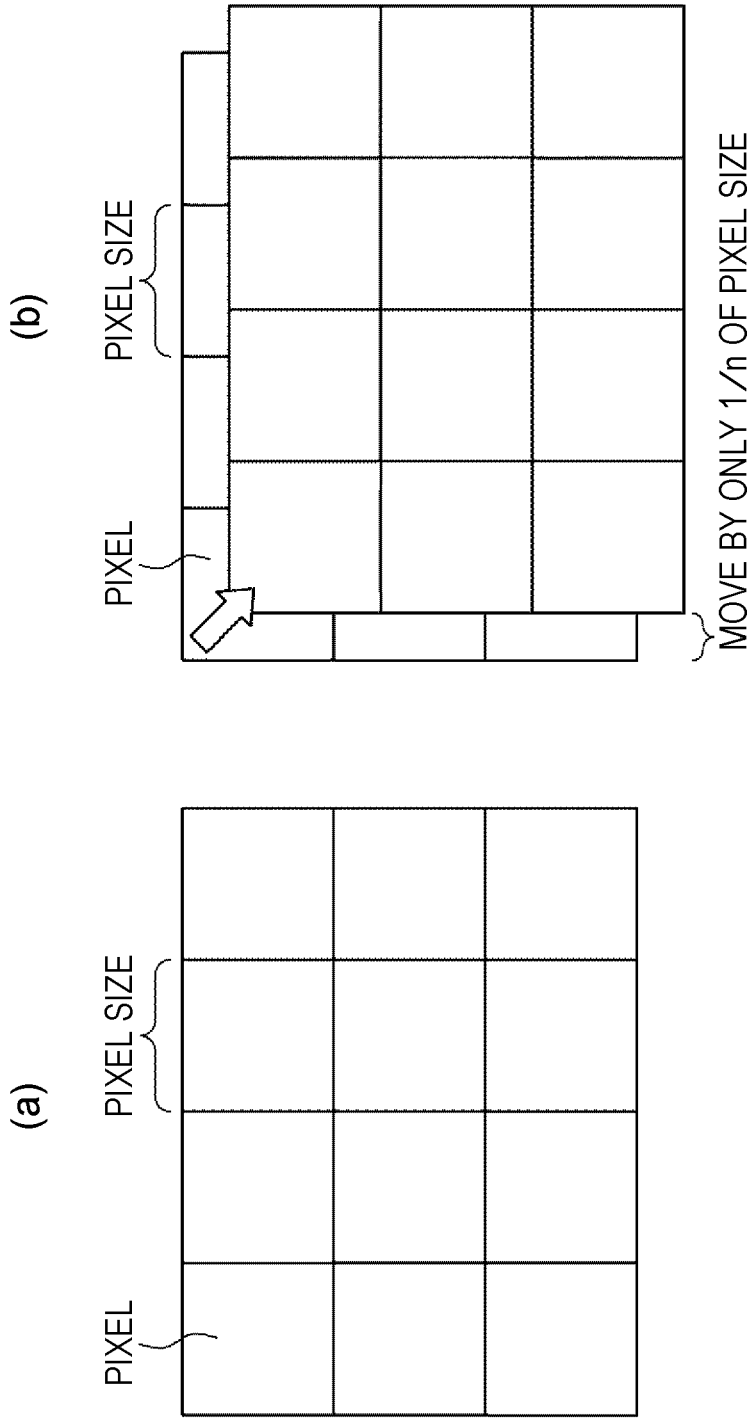
FIGS. 4(a) and 4(b) are diagrams specifically illustrating movement of an image detector in the present invention.

FIG. 4(a) is a diagram illustrating pixels constituting an image detector and a pixel size. In this drawing, the image detector is divided into four equal parts in a lateral direction (X-direction). FIG. 4(b) is a diagram explaining movement of image detector. As illustrated in the drawing, the image detector is moved for each half rotation, in each of directions (X-direction and Y-direction) by only a distance obtained by dividing the pixel size into n equal parts (1/n of the pixel size) (n is a natural number excluding 1). Here, 1/n of the pixel size corresponds to the moving distance d illustrated in FIGS. 3(a) and 3(b). Accordingly, the number of movement is n−1, and the number of image groups Im to be obtained is n. Here, an upper limit of n is determined based on a balance between required image resolution and measurement time for obtaining images in accordance with the number of movement of the image detector.

Figure 5:
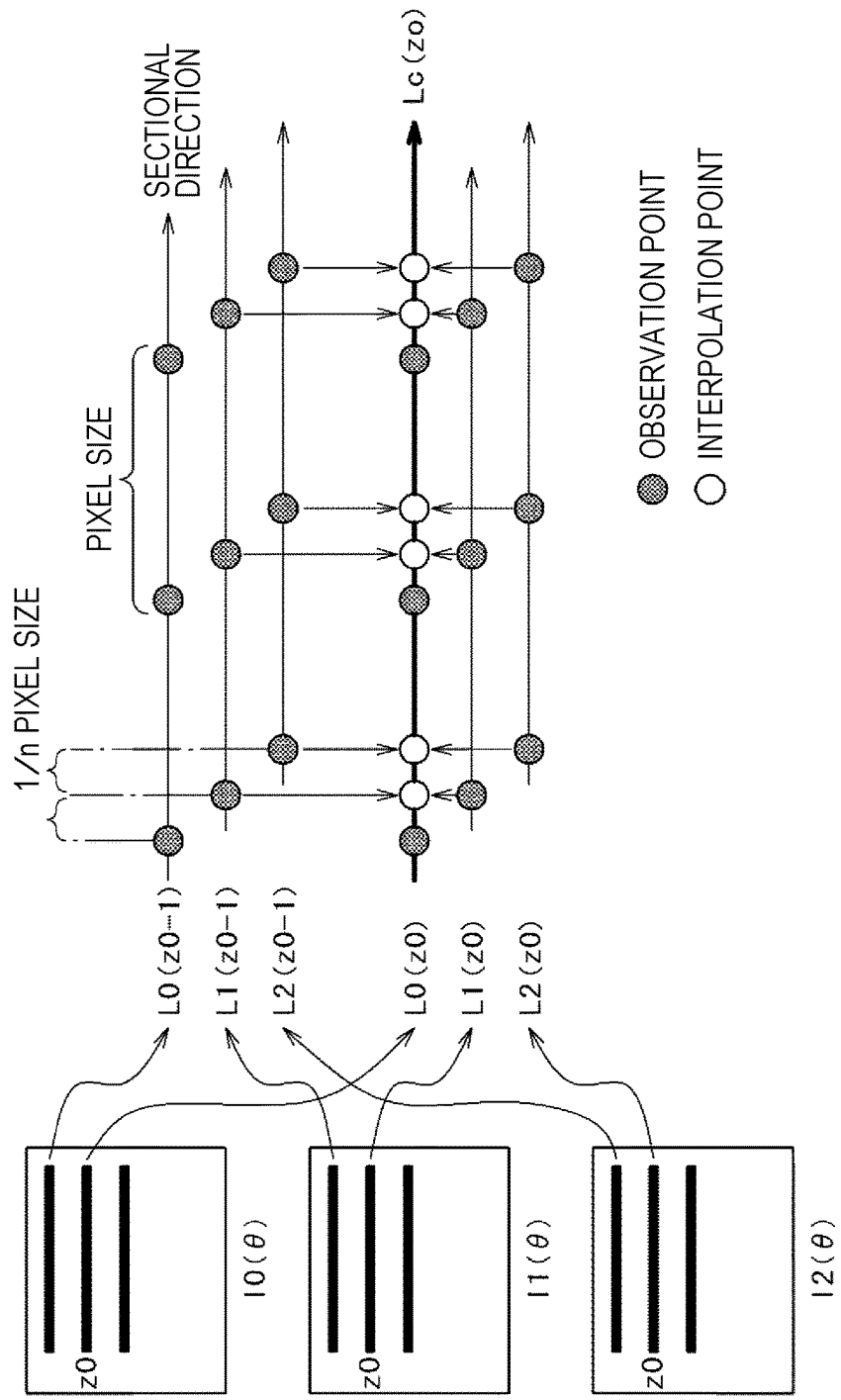
FIG. 5 is a diagram specifically illustrating an image synthesis method according to the present invention.

A sinogram can be synthesized from the obtained image groups Im by a method illustrated in FIG. 5. With the use of an image Io at the initial position of the detector as a reference, intervals between the pixels thereof are filled with data of the image groups Im through linear interpolation.

First, diagrams illustrated in the left side part of FIG. 5 illustrates image groups Im constituted by pixel lines including a plurality of pixels. In the drawing, three pixel lines are exemplified, and three images are illustrated. For example, a reference pixel line among the pixel lines in the image illustrated in the top row is denoted by z0, a projection angle of the image is denoted by θ, and a position coordinate of a representative point of the image in a sectional direction is denoted by x. In addition, when the image groups Im sequentially illustrated from the top row to downward rows thereof are denoted by $I_0$, $I_1$, and $I_2$, respectively, $I_1$ is an image obtained by moving the detector by only 1/n of the image size with respect to $I_0$, and $I_2$ is an image obtained by moving the detector by only 1/n of the image size with respect to $I_1$.

As with the case of $I_0$, the images $I_1$ and $I_2$ are obtained at the projection angle θ, and therefore, as with the case of $I_0$ (θ), the images are denoted by $I_1$ (θ) and $I_2$ (θ), respectively. Next, a method for obtaining a synthesized image from the image groups $I_0$ (θ), $I_1$ (θ), and $I_2$ (θ) will be described.

First, when a line profile of a reference image $I_0$ at a projection angle θ in z0 is denoted by Lo (θ, z0, x), and a corresponding line profile of an image group Im is denoted by Lm (θ, z0, x), . . . , a synthesized line profile Lc (θ, z0, x) can be obtained as the following (Formula 1).

[Mathematical Formula 1]

$$Lc(\theta, z0, x+m/n) = (1-m/n)Lm(\theta, z0, x) + (m/n)Lm(\theta, z0-1, x)$$ (Formula 1)

The synthesized line profile Lc will be described in detail below using FIG. 5.

Line profiles corresponding to pixel lines of a pixel $I_0$ ($\theta$) is Lo (Z0−1) and Lo (Z0) from the top row. Similarly, line profiles corresponding to pixel lines of a pixel $I_1$ ($\theta$) is $L_1$ (Z0−1) and $L_1$ (Z0) from the top row, and line profiles corresponding to pixel lines of a pixel $I_2$ ($\theta$) is $L_2$ (Z0−1) and $L_2$ (Z0) from the top row.

In a pixel line of a synthesized line profile Lc (z0) indicated by a bold line in the drawing, observation points are formed of Lo (Z0), and interpolation points are formed from synthesis of $L_1$ (Z0−1) with $L_1$ (Z0), or that of $L_2$ (Z0−1) with $L_2$ (Z0).

When the same synthesis is performed and the interpolation points are filled, the number of pixels of Lc increases to n times as many as that of Lm. Then a sinogram is generated by arranging the line profile Lc (z0) in z0 synthesized at each projection angle θ in order of θ, and a sectional image is reconstructed with the sinogram. Subsequently, processing which uses Im instead of Io as a reference image is sequentially performed similarly, and thereby an image with high spatial resolution in both the sectional and rotation axis directions can be obtained. Data synthesized by the processing, when it is thought to be a projection image at a projection angle θ, is an image formed of small data obtained by two-dimensionally dividing the pixel size into n equal parts. With the use of the data, a sectional image having high spatial resolution is reconstructed.

Figure 6:
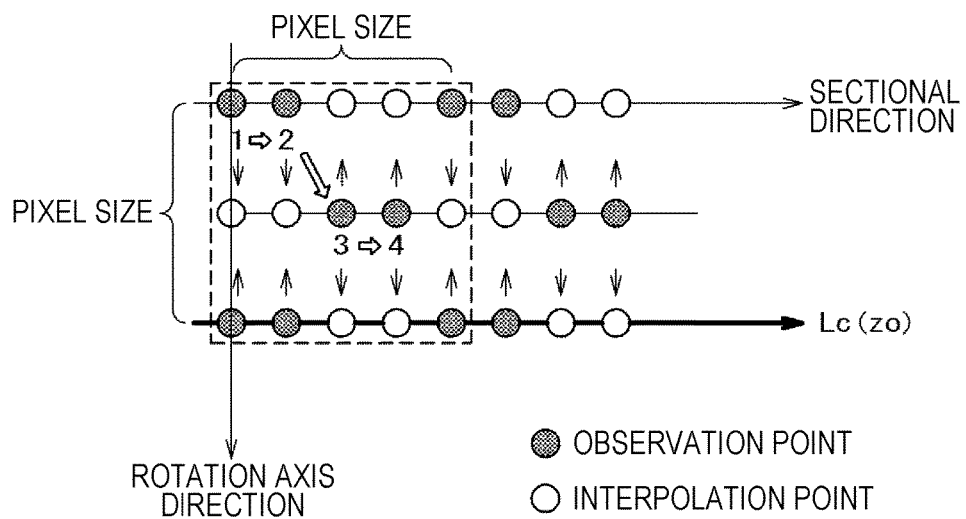
FIG. 6 is a diagram specifically illustrating an image synthesis method according to the present invention.

FIG. 6 is a diagram illustrating an image synthesis method different from that illustrated in FIG. 5.

Open arrows indicate a direction of movement of the detector. Numbers in the drawing indicate the order of movement. Solid arrows indicate a direction of synthesis.

When the detector is moved in such a manner that, as illustrated in FIG. 6, a movement width in a rotation axis direction is adjusted to be large and the detector is moved in the rotation axis direction only once while the detector is moved in a sectional direction a plurality of times, the number of data points in a synthesized image is larger in the sectional direction than in the rotation axis direction. Therefore, an image having higher spatial resolution in the sectional direction can be reconstructed.

Figure 7:
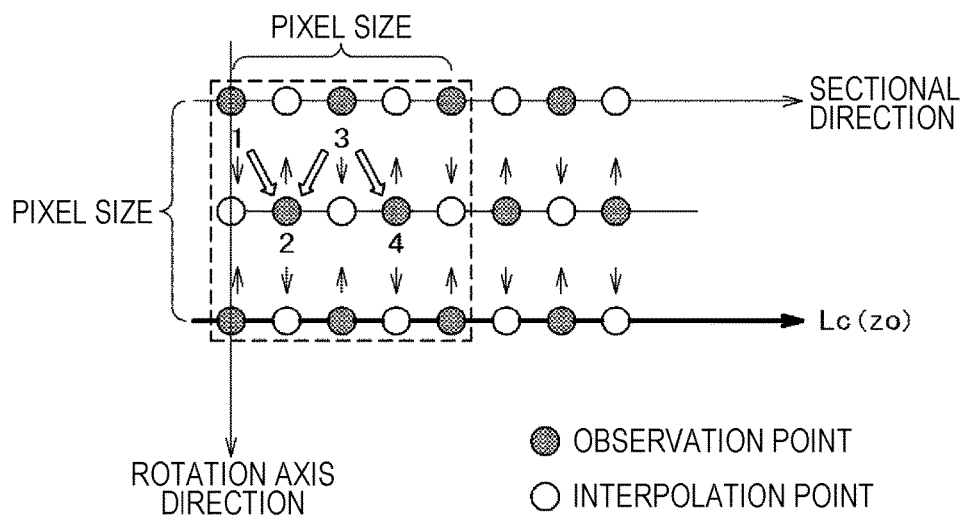
FIG. 7 is a diagram specifically illustrating an image synthesis method according to the present invention.

FIG. 7 is a diagram illustrating an image synthesis method different from those illustrated in FIGS. 5 and 6.

Open arrows indicate a direction of movement of the detector. Numbers in the drawing indicate the order of movement. Solid arrows indicate a direction of synthesis.

The detector is not sequentially moved in the same direction, but moved in a zig zag manner as illustrated in FIG. 7. Consequently, a sinogram can be generated in which observation points are uniformly distributed, which makes possible to reconstruct a more accurate sectional image. On the other hand, when an increment of movement in an in-plane direction is adjusted to be large and an increment in a rotation axis direction is adjusted to be small contrary to the above cases, an axial image having higher spatial resolution than a sectional image can be reproduced contrary to FIGS. 6 and 7.

Figure 8:
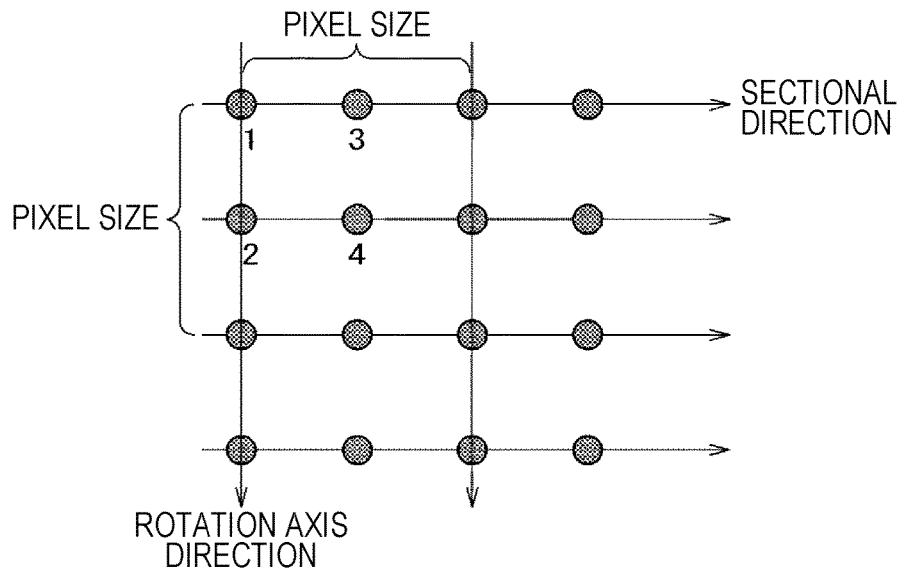
FIG. 8 is a diagram specifically illustrating an image synthesis method according to the present invention.

In a case where there is no limitation for a measurement time and radiation exposure, when the measurement is performed at all points between the pixels as illustrated in FIG. 8, all points can be filled with observation points, which makes possible to reproduce a more accurate image.

In a case where the intensity of incident X-rays is varied with time or where the sensitivity of the detector is not constant, when image groups are synthesized as they are based on the above manner, division processing with a background image cannot be performed sufficiently, which causes in occurrence of cyclic fine artifacts with a period of the pixel size (the number of divided portions). In this case, the synthesis is preferably performed after integrating intensities (counted values) of all elements for each image group Im, and multiplying each image group by a coefficient according to a ratio with respect to an image I0 at the initial position. By doing so, variations of the intensity of incident X-rays or instability of detection sensibility is canceled, and an image having less artifacts and higher definition can be obtained. In addition, there may be a case where a sectional image is reconstructed separately from each of the image groups Im, an average CT value in a region of several tens of pixels is obtained for each reproduced image, and then a synthesis ratio is obtained from the ratio of the average CT values. Furthermore, there may be a case where a sinogram is generated from each of the image groups Im, intensities are integrated for a line of each angle, and thereby a synthesis ratio is obtained.

First Embodiment

Figure 9:
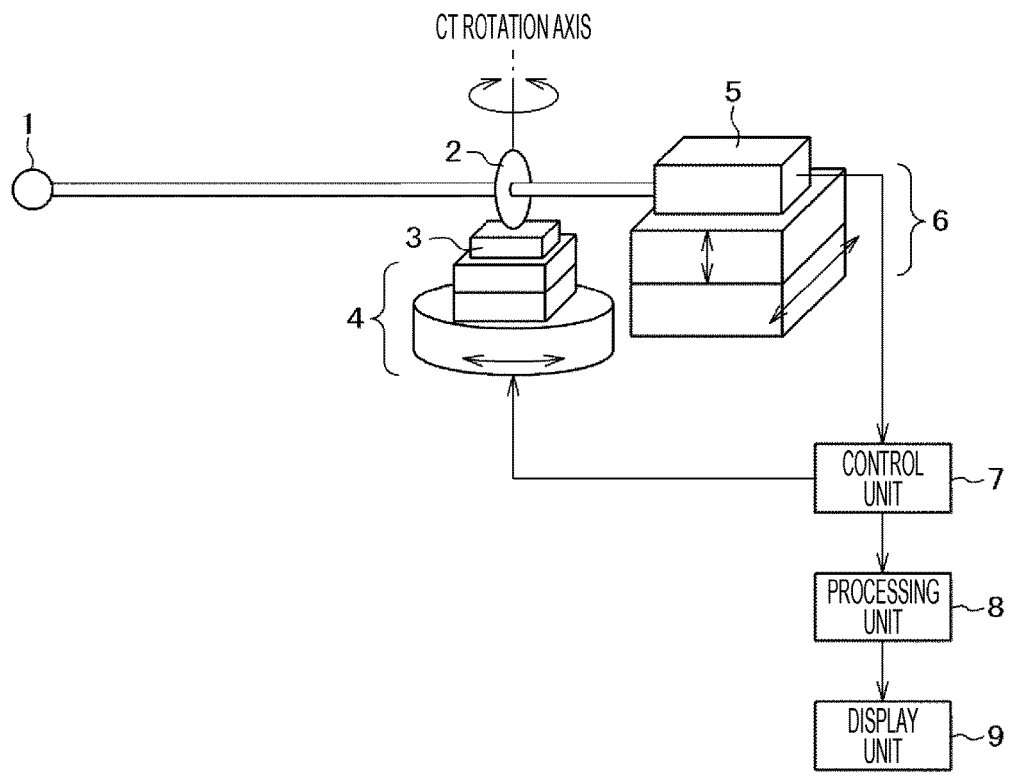
FIG. 9 is a diagram illustrating a configuration of a apparatus according to a first embodiment.

FIG. 9 is a diagram illustrating a configuration of an example of an X-ray imaging apparatus used in the present invention. As illustrated in the drawing, the X-ray imaging apparatus consists of an X-ray source 1, a subject 2, a subject holder 3, a subject rotation-positioning table 4, an X-ray image detector 5, an image detector positioning table 6, a control unit 7, a processing unit 8, and a display unit 9.

The subject 2 held by the subject holder 3 is irradiated with an X-ray (illustrated by a double line in the drawing) emitted from the X-ray source 1. The subject holder 3 is attached to the subject rotation-positioning table 4, and an irradiation position and an irradiation angle are adjusted by the table 4. The intensity of the X-ray transmitted through the subject 2 is detected by the X-ray image detector 5 positioned by the image detector positioning table 6. The control unit 7 rotates a specimen and positions the detector in accordance with a measurement procedure described later, and performs imaging. The processing unit 8 synthesizes a sinogram from each of the obtained projection images, and reproduces a sectional image of the specimen through reconstruction calculation. The display unit 9 displays each image obtained in the processing unit 8.

In the apparatus, under the control of the control unit 7, a sectional image of the subject 2 is measured in accordance with the following procedure (see FIG. 2(b)).

1) The subject 2 is arranged to be positioned at the center of an X-ray beam by the subject rotation-positioning table 4.

2) The projection angle is reset to 0 degrees with respect to the subject 2.

3) The position of the X-ray image detector 5 is set to the origin by the image detector positioning table 6.

4) The subject 2 is rotated by the subject positioning rotation table 4 in increments of a predetermined angle, and at each angle of rotation, a projection image is detected by the X-ray image detector 5.

5) The step described in 4) is repeated until the angle of rotation of the subject reaches 180 degrees.

6) When the angle of rotation has reached 180°, the X-ray image detector 5 is two-dimensionally moved to a predetermined position by the image detector positioning table 6.

7) The steps described in 4) to 6) are repeated a predetermined number of times, and projection image group data Im at each position of the detector is obtained.

A sectional image is reconstructed from the image groups thus obtained by synthesizing a sinogram by the above-described method, and then performing reconstruction calculation using filtered back projection (FBP), iterative projection, or the like.

As described above, the X-ray image detector 5 is usually positioned by moving the detector by only 1/n of the pixel size along each axis as illustrated in FIG. 4(b), and repeating the steps described in 4) to 6) n times. In a case where a sectional image having high spatial resolution is required, stepwise movement may be employed in a rotation axis direction as illustrated in FIGS. 6 and 7 to obtain a data group having small increments in a sectional direction.

On the other hand, in a case where an image having high resolution in a rotation axis direction is required, the detector may be minutely moved in a rotation axis direction. In addition, in a case where there is no significant limitation for a measurement time, and an image having high resolution in either directions is required, two-dimensional scanning may be performed with the X-ray detector for each half rotation of the subject as illustrated in FIG. 8 to obtain CT data sets at all interpolation points. With regard to the selection of these modes, for example, an operator may select on the spot on the display apparatus 9.

Figure 10:
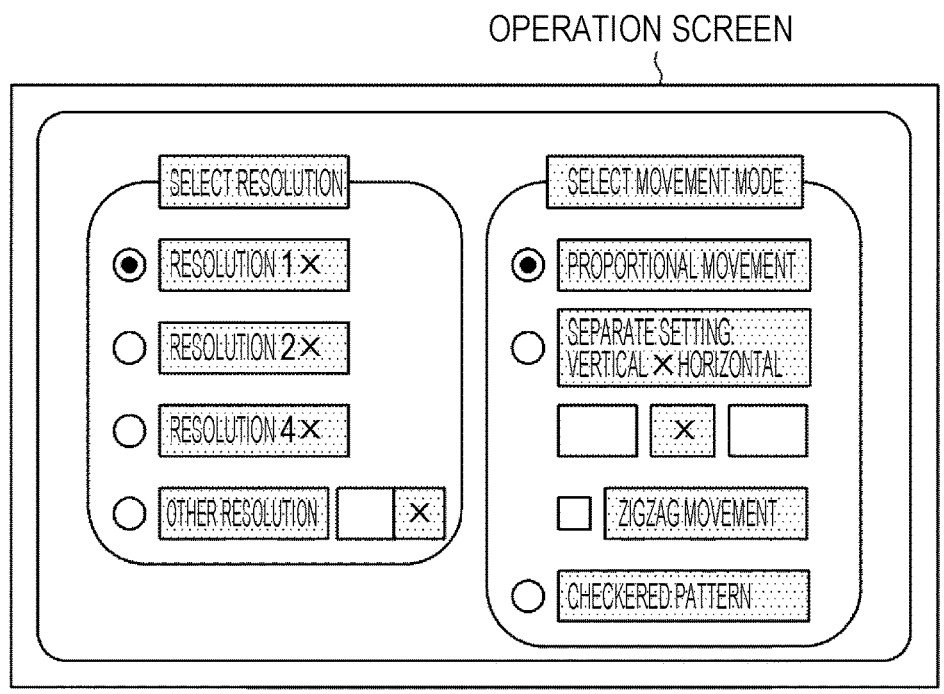
FIG. 10 is a view illustrating an operation screen shot according to the first embodiment.

FIG. 10 illustrates an example of an operation screen displayed on the display apparatus 9. On the screen, required resolution can be selected. In a case where higher resolution is required than a reference resolution (1×), the displayed magnification (2×, 4×, or other magnifications) can be selected.

In addition, a detector movement mode can be selected on the screen. Examples of movement modes which can be selected includes a proportional movement mode, a movement mode in which vertical and horizontal moving distances are separately set, and a checkered pattern movement mode. The operator can select any of the movement modes on the spot.

As the X-ray image detector 5, those directly detecting an incident X-ray, such as a flat panel and a back-illuminated CCD, may be used. In this case, the size of an pixel is fixed. However, the X-ray can be detected with a high efficiency. In addition, other type of detectors may be used in which an incident X-ray is converted into an electron or visible light by a phosphor, and then the incident X-ray is detected with an imaging element. Examples thereof include an X-ray II (image intensifier) and a lens coupling-type detector. The magnification of a lens system can be changed, and an X-ray can be detected at arbitrary magnification. The detector is not irradiated with an X-ray, and therefore, damage can be significantly reduced in comparison to direct type detectors. Furthermore, depending on the measurement condition, the thickness and the type of the phosphor can be changed to perform detection under an optimum condition.

As the image detector positioning table 6, a general positioning table driven by a motor may be used. When a stepping motor is used as a driving motor, positional accuracy is excellent and positional accuracy in the order of a fraction of the pixel size can be easily achieved. Even when the image detector is a little heavy, positioning can be performed properly. Alternatively, a piezoelectric element (PZT) can be used as a driving table of the positioning table. The PZT expands and contracts by several tens to several hundreds of micrometers when a voltage is applied thereto, and operation time thereof is 100 ms, which means that the PZT has a remarkable characteristic of high speed. Therefore, the PZT can position an image pixel in a period of time shorter than 1/10 of the time required in a case where the positioning table is driven by a motor. However, the withstand load thereof is relatively small. Therefore, it may be determined which type of the stages is employed in consideration of the size and the weight of the image detector.

As described above, according to the embodiment of the present invention, a subject image having high spatial resolution can be reconstructed by performing measurements while changing the position of the image detector for each half rotation of the subject, and synthesizing image groups thus obtained.

Second Embodiment

In the first embodiment, since the X-ray image detector 5 which has no energy resolution is used, elemental information of the subject cannot be obtained. In this embodiment, description will be given regarding an example which uses an imaging element capable of arbitrary setting a detectable lowest energy (hereinafter referred to as threshold energy) for each element.

Figure 11:
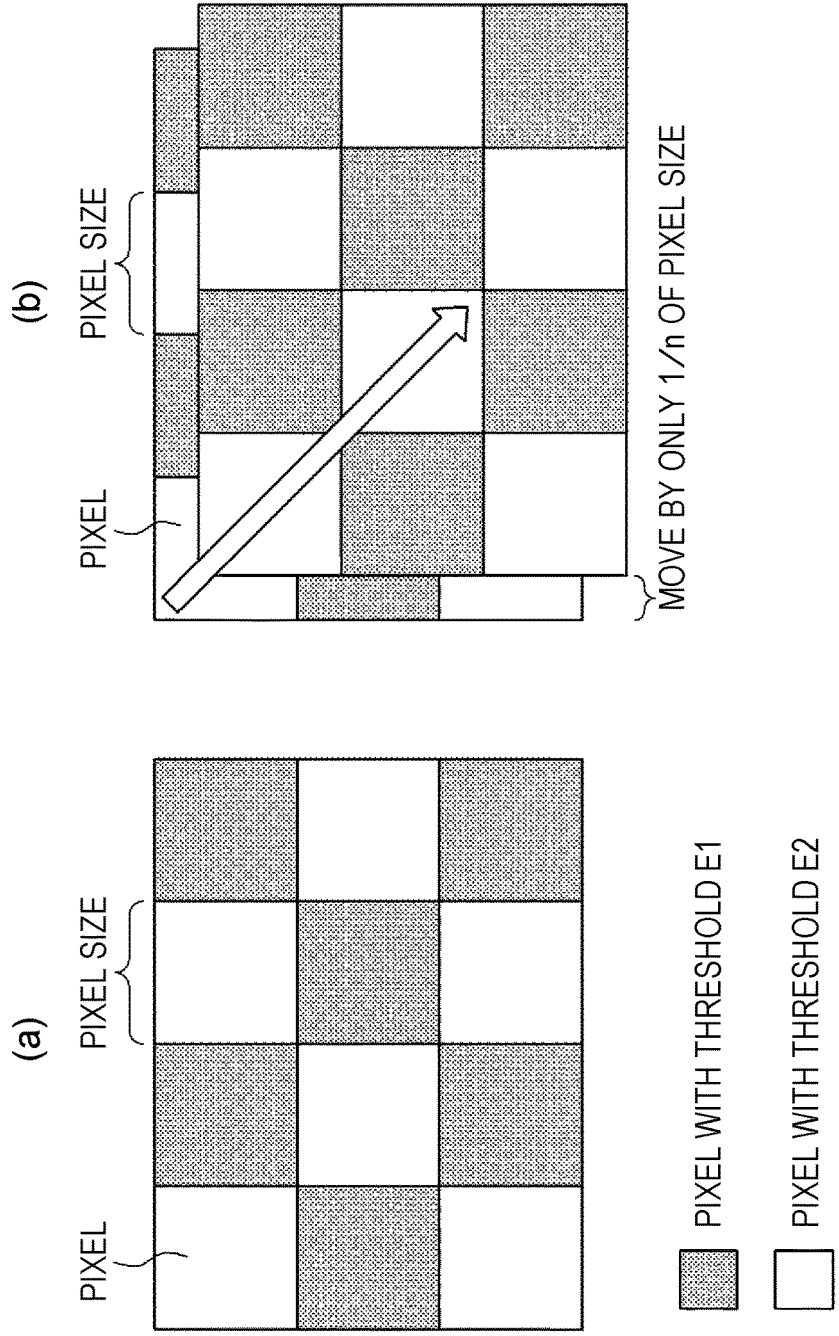
FIGS. 11(a) and 11(b) are diagrams illustrating examples of a configuration of an energy threshold of an image detector according to a second embodiment, and movement method thereof.

FIGS. 11(a) and 11(b) illustrate an example of setting of each threshold energy in the detector according to the embodiment. Here, in order to simplify the description, an example using two threshold energies is described. However, even when three or more threshold energies are used, arrangement, measurement, and data processing may be performed in a similar manner.

In FIGS. 11(a) and 11(b), black elements (dotted) are elements with a low threshold energy (E1), and white elements (white) are elements with a high threshold energy (E2). The black and the white elements are alternately arranged in a checkered pattern. The measurement procedure is as follows. As with the case of the first embodiment, the detector is moved by the image detector positioning table 6 along both axes by only 1/n of the pixel size for each half rotation of a subject, and then imaging is performed. However, the number of measurements is not n, but 2n. In other words, the measurement is performed until the moving distance of the detector reaches twice as large as the pixel size.

When extracting only E1 pixels in an obtained transmission image, an interval between the pixels is twice as large as the pixel size. Therefore, an image is synthesized here based on a formula obtained by adjusting (Formula 1) to be applicable to the interval twice larger than the pixel size. By doing so, an X-ray image having at least the energy E1 can be obtained at the pixel size 1/n in the same manner as in the first embodiment. By processing E2 pixels similarly, an image having at least the energy E2 can be obtained. A ratio of absorption occurring when the energy is changed from E1 to E2, in other words, a ratio of absorption coefficient, can be calculated by performing division for each pixel in the two images.

Figure 12:
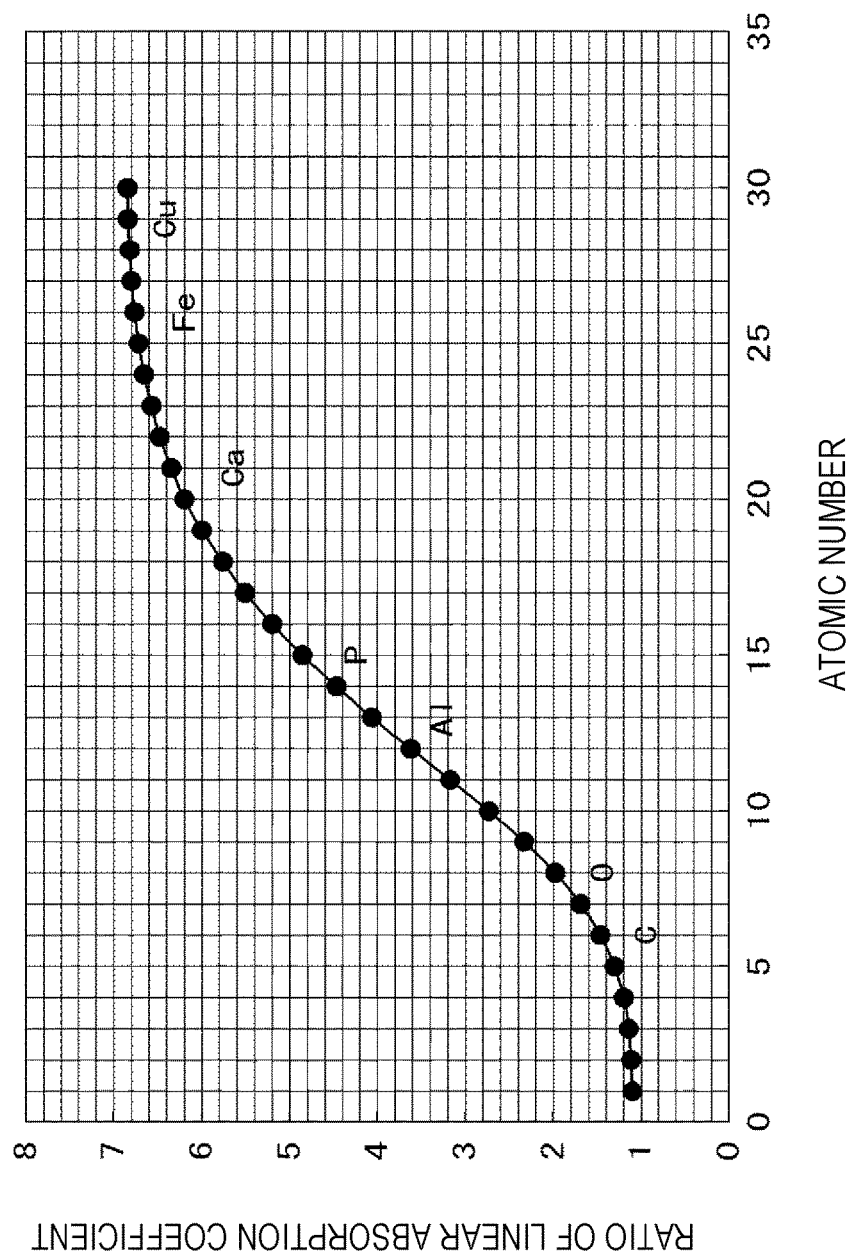
FIG. 12 is a graph illustrating a relation between ratios of absorption coefficient and atomic numbers.

FIG. 12 illustrates a chart of calculated a relation between the ratios of absorption coefficient and atomic numbers. As illustrated in the calculation example of the drawing, the ratios of absorption coefficient depend on atomic numbers, and correspond thereto on a one-to-one basis. In other words, when the subject is constituted with a single element, the kind of the element can be estimated from the element number, and when the subject is constituted with a plurality of elements, an average element number (effective atomic number) can be calculated. Therefore, elemental information can be obtained without using other detection methods, such as X-ray fluorescent method, and an absorption edge method.

As described above, according to the embodiment of the present invention, elemental information of the subject can be obtained with high resolution by using the X-ray image detector capable of setting a threshold energy.

Third Embodiment

In the first and the second embodiments, variations of the intensity of X-rays are imaged, which variations have occurred when X-rays have been transmitted through the subject. Consequently, soft tissue of biomedical organisms, an organic material, and the like, which are constituted mainly by light elements with less absorption, cannot be observed with high definition. Here, an embodiment will be described in which an X-ray is captured as a wave, and a phase changes (phase shift) of the X-ray caused by a subject is imaged. There is a characteristic that in a hard X-ray region, a cross-section of phase shift is 1000 or more times larger than a cross-section of absorption for light elements. Accordingly, a measurement can be performed with high sensitivity by using the phase shift.

The phase shift cannot be directly detected with the current technology. Therefore, in order to detect the phase shift, it is necessary to convert the phase shift into a detectable intensity of X-rays by using an X-ray optical element and the like. As a method for the conversion, the following methods have been developed: (1) X-ray interferometry using an X-ray interferometer, (2) a diffraction contrast method with which refraction of X-rays is detected by X-ray diffraction, (3) Talbot interferometry using a Talbot interferometer, and (4) a propagation method using Fresnel fringes. Among these, the Talbot interferometry has a remarkable characteristic that the method can be performed with a diverging beam, in other words, with an X-ray source used in laboratories. In addition, it has a wide dynamic range with respect to density, and even a composite material can be measured which includes metal and an organic material in combination.

Hereinbelow, a case where the Talbot interferometry is used will be described in the embodiment.

Figure 13:
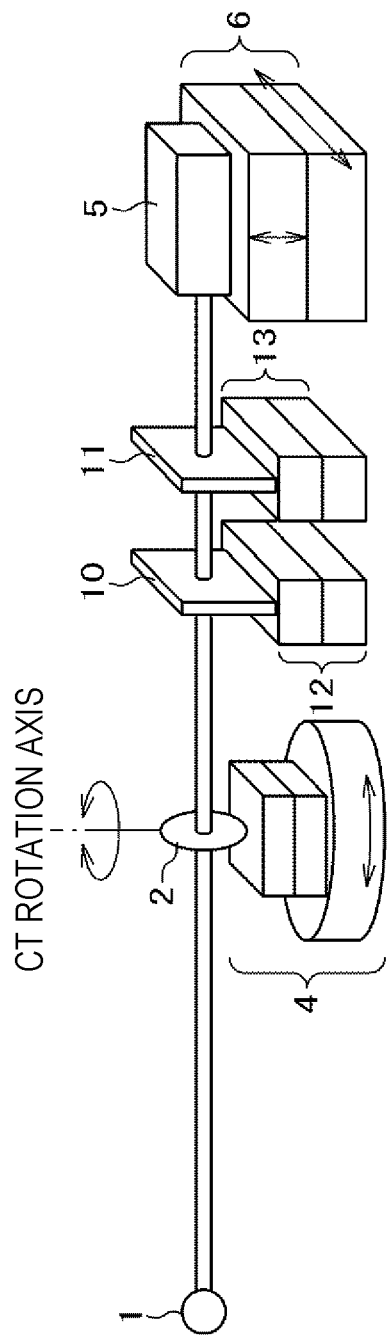
FIG. 13 is a view illustrating an example of a apparatus configuration according to a third embodiment.

The Talbot interferometer consists of two X-ray diffraction gratings (a component in which regions having different X-ray transmittance are formed in a grating shape), which are a phase grating (G1) 10 and an absorption grating (G2) 11. Accordingly, also in the present invention, the phase grating (G1) 10 and the absorption grating (G2) 11 are set between a subject and an image detector as illustrated in FIG. 13, and an interference fringe caused by the interferometer is obtained by the image detector. Quantitative detection of the phase shift is obtained by relatively moving the (G1) 10 to the (G2) 11 by only 1/n (n is an integer of 3 or greater) of the interval of the diffraction gratings, and performing calculation using a plurality obtained interference images. When an interference image obtained in an m-th measurement is denoted by Im, a phase shift $\varphi$ can be calculated with the following (Formula 2).

[Mathematical Formula 2]

$$\phi = \tan^{-1}\left(\frac{\sum_{m=0}^{n-1} Im \sin\frac{2\pi m}{n}}{\sum_{m=0}^{n-1} Im \cos\frac{2\pi m}{n}}\right) \quad \text{(Formula 2)}$$

Figure 14:
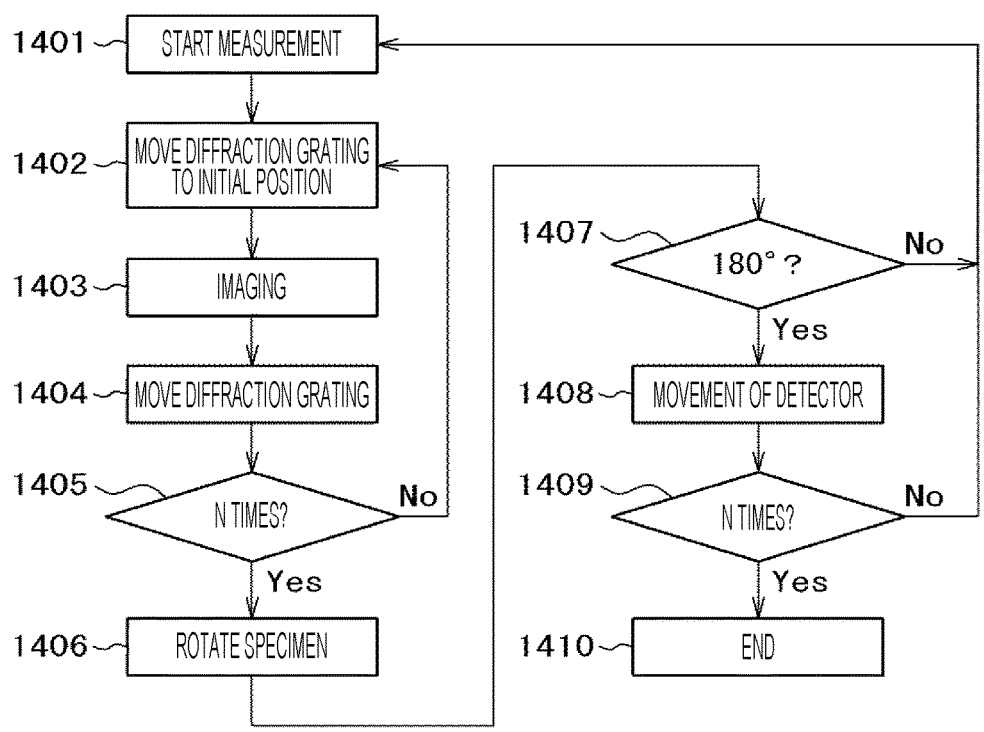
FIG. 14 is a chart illustrating an example of a flow of measurement procedure according to the third embodiment.

In addition, since the phase shift $\varphi$ is in proportion to a spatial phase differential amount of the subject, a spatial distribution of the phase shift, in other words, a density distribution image can be obtained by integrating the obtained phase shift image in the direction parallel to the direction in which the (G1) 10 and the (G2) 11 relatively scanned. Therefore, FIG. 14 shows the flow chart of the measurement procedure. In other words, it is a flow obtained by adding a step of performing a fringe scanning method to the flow of control illustrated in FIG. 2(b). Other measurement procedures described above are the same as those in the first embodiment.

As the phase grating (G1) 10, those having an interval between grids of several micrometers and a difference in a thickness between grids with which a phase of an X-ray is shifted by ¼ or ½ wavelength are used. As the absorption grating (G2) 11, those having an interval between grids of several micrometers and one of the grids has a thickness with which an X-ray is completely absorbed are preferable. However, it is difficult to manufacture such a grating since a thickness of several tens of micrometers or more is required even if gold is used. Therefore, a little thin diffraction grating (difference in transmittance among grids is about 30% or greater) may be used. However, in this case, since visibility of the interference image is lowered, density resolution is lowered accordingly. The (G1) 10 and the (G2) 11 are positioned by the rotation positioning tables 12 and 13, respectively. On that occasion, when a shaft used for fringe scanning is driven by a PZT to achieve high-speed scanning, data can be obtained in a shorter measurement time.

As described above, according to the embodiment of the present invention, a high resolution observation can be performed for a subject with high density resolution by using a Talbot interferometer.

Fourth Embodiment

Figure 15:
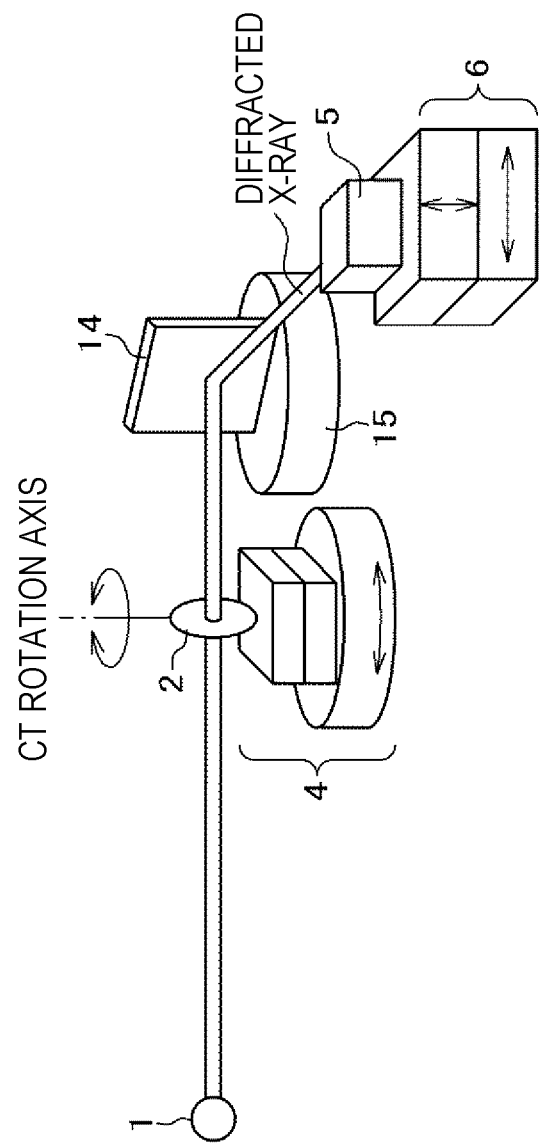
FIG. 15 is a view illustrating an example of a apparatus configuration according to a fourth embodiment.

In the third embodiment, Talbot interference has been used for phase detection. In this embodiment, an example using a diffraction contrast method will be described. FIG. 15 is a view illustrating an embodiment of the present invention. In comparison to the configuration in the first embodiment illustrated in FIG. 9, one analyzer crystal 14 is disposed downstream a subject 2, and an X-ray image detector 5 is disposed at a position where an X-ray diffracted by a single crystal plate of the analyzer crystal 14 is detected.

Figure 16:
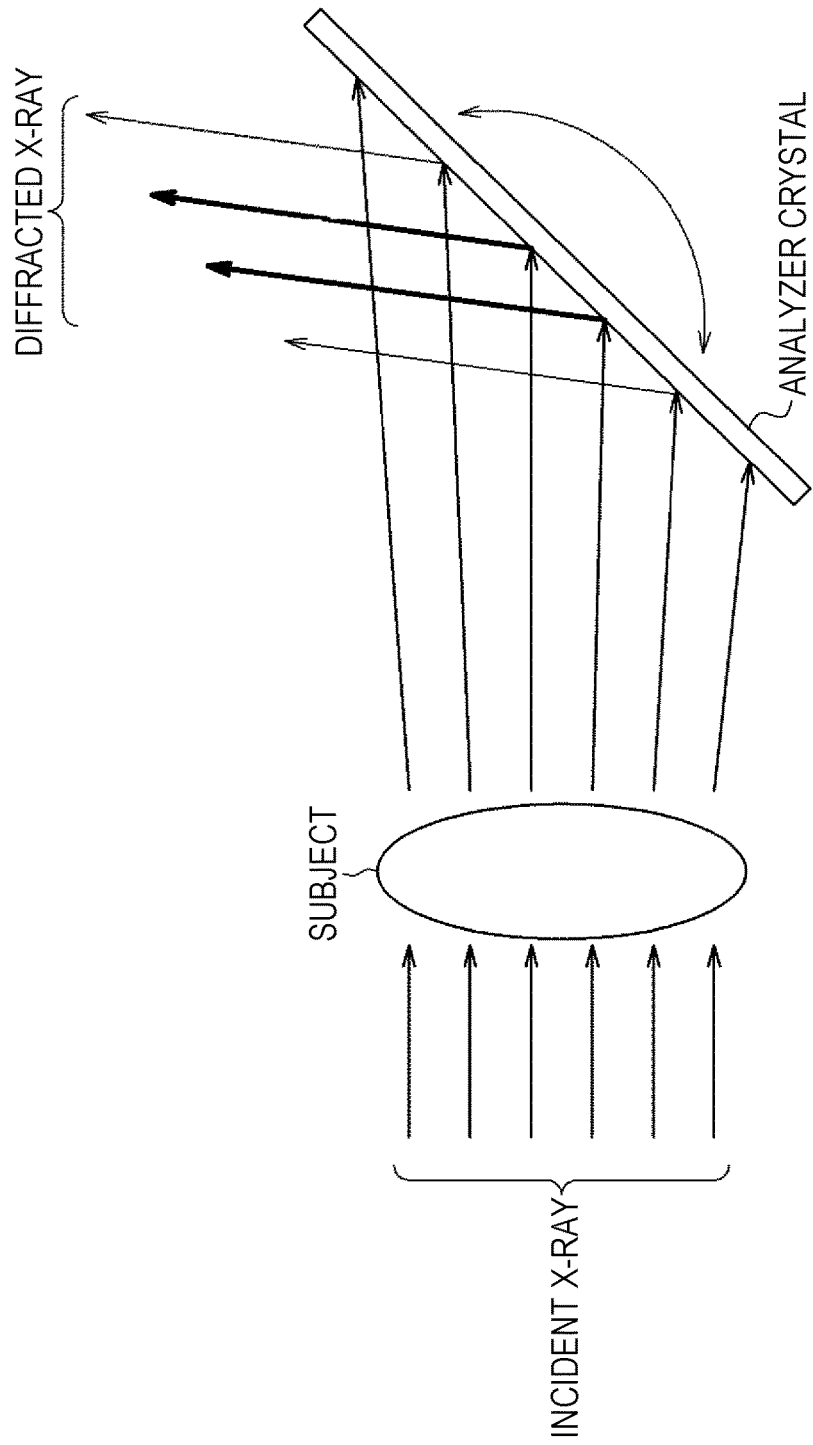
FIG. 16 is a diagram illustrating X-ray diffraction and intensities thereof.

FIG. 16 illustrates X-rays diffracted by the analyzer crystal and intensities thereof. Regarding the diffracted X-ray, only X-ray having an angle which satisfies a Bragg condition with respect to the analyzer crystal is reflected. The difference in intensities of the diffracted X-rays thus reflected is indicated by the thickness of the lines in the drawing.

In a case where a spatial differential amount of density is large when an X-ray is transmitted through the subject 2, a travelling direction of the X-ray is bent by refraction as illustrated in FIG. 16. In X-ray diffraction with a single crystal, an angle width of an incident X-ray which causes diffraction is extremely narrow, and is several arcseconds at most. Therefore, when the angle of the incident X-ray is adjusted to cause diffraction without a subject, the refracted X-ray no longer satisfies the diffraction condition, and thereby the intensity of the diffracted X-ray is extremely weakened (FIG. 16). With the use of this phenomenon, refraction caused by a subject, in other words, spatial differential of density can be detected with high sensitivity.

In addition, the density can be obtained with extremely high sensitivity by performing integration in the same manner as in the Talbot interferometry.

In order to quantitatively obtain a differential amount of a phase shift from intensities of diffracted X-rays, the analyzer crystal is rotated by a minute angle with respect to incident X-rays as illustrated in FIG. 16, and an intensity at each rotation angle (rocking curve) is measured. A refraction angle, in other words, a differential amount of a phase shift in each pixel can be obtained from a "shift" from the central position of the curve. The "shift" from the center may be obtained by regression of the rocking curve with respect to Gaussian function or the like, or may be obtained from the center of each data point. Accordingly, a control flow thereof is almost the same as that of the third embodiment, and the measurement includes scanning of crystal angles in the innermost loop.

Figure 17:
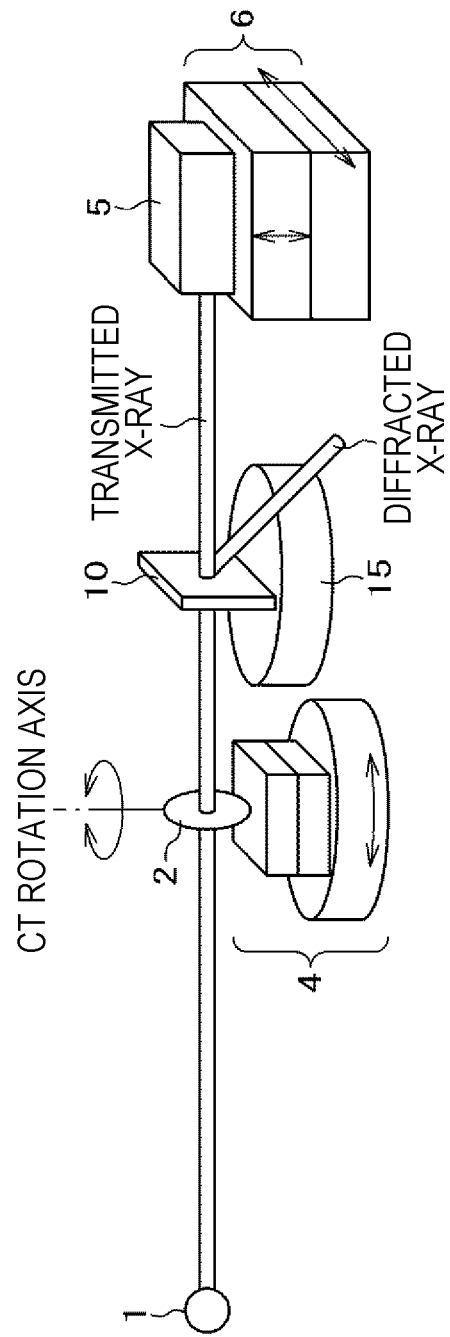
FIG. 17 is a view illustrating an example of a apparatus configuration according to the fourth embodiment.

There is a transmission-type X-ray diffraction (Laue case) other than the reflection-type X-ray diffraction (Bragg case). FIG. 17 illustrates a configuration example of a apparatus for performing transmission-type X-ray diffraction. In comparison to the apparatus for reflection-type X-ray diffraction illustrated in FIG. 15, an X-ray image detector 5 is disposed differently. In this configuration, the X-ray image detector 5 is disposed at a position where an X-ray transmitted through a single crystal plate of an analyzer crystal 14 is detected.

In the Laue case, since an intensity of a transmitted X-ray also varies depending on an incident angle, as with the Bragg case, a refraction angle caused by a subject, in other words, a spatial differential amount of density, can be detected from the variation in the intensity. In the Laue case, since an X-ray enters the analyzer crystal at an angle nearly perpendicular thereto, a wider field of view can be secured with the crystal of the same size, in comparison to the Bragg case. In addition to the transmitted X-ray, a diffracted X-ray exhibits similar variations in intensity depending on a refraction angle. Therefore, it is also possible to use this X-ray for imaging. Furthermore, when an image detector with a wide field of view or two image detectors are used so that both beams can be observed at the same time, imaging in a shorter period of time or imaging with high sensitivity can be performed.

As the analyzer crystal 14, those cut out from a silicon ingot may be used. Regarding crystal orientation for diffraction, the effect of crystal strain caused by processing can be reduced by using basic Si (111) or (220). In a case where the energy of an X-ray exceeds 50 keV, a larger diffraction angle is obtained when using (311), (440), or the like, which is a higher-order diffraction plane, and therefore, the crystal size can be reduced. An analyzer crystal angle-adjustment table 15 which adjusts the angle of the crystal is required to have high positional accuracy of $1/100$ seconds or greater. Therefore, a rotating goniostage using a tangential bar or the like may be used.

As described above, according to the embodiment of the present invention, a subject can be observed with high density resolution by using a refraction contrast method.

REFERENCE SIGNS LIST

1 X-ray source
2 subject
3 subject holder
4 subject rotation-positioning table
5 X-ray image detector
6 image detector positioning table
7 control unit
8 processing unit
9 display unit
10 phase grating (G1)
11 absorption grating (G2)
12 phase grating rotation-positioning table
13 absorption grating rotation-positioning table
14 analyzer crystal
15 analyzer crystal rotation-positioning table

The invention claimed is:

1. An X-ray imaging apparatus comprising:
an X-ray generation unit that generates an X-ray and irradiates a subject with the X-ray;
a subject positioning rotation table unit that adjusts an angle of the subject with respect to an optical path direction of the X-ray and an incident position of the X-ray to the subject;
an X-ray image detection unit that detects an X-ray transmitted through the subject;
a detector positioning table unit that two-dimensionally moves and positions the X-ray image detection unit on a surface perpendicular to an X-ray;
a processing unit that calculates a sectional image of the subject from a plurality of X-ray images obtained by moving the X-ray image detection unit by the detector positioning table unit; and
a control unit that controls each of the units, wherein
the X-ray image detection unit obtains an X-ray image while an angle of the subject with respect to the optical path direction of the X-ray is changed by the subject positioning rotation table unit,
the detector positioning table unit moves the X-ray image detection unit for each time the angle reaches half rotation, and
the moved X-ray image detection unit repeatedly obtains the X-ray image.

2. The X-ray imaging apparatus according to claim 1, wherein a motion axis of the detector positioning table unit includes two axes perpendicular to each other, and the two axes are in a plane perpendicular to an incident X-ray upon the X-ray image detector.

3. The X-ray imaging apparatus according to claim 2, wherein a moving distance of the detector positioning table unit varies for each motion axis.

4. The X-ray imaging apparatus according to claim 1, wherein the moving distance of the detector positioning table unit is 1/n (n is a natural number excluding 1) of a size of a pixel that constitutes the X-ray image detector.

5. The X-ray imaging apparatus according to claim 1, wherein an X-ray diffraction grating, in which regions having different X-ray absorptivity are alternately arranged in a grating shape, is disposed between the subject and the X-ray image detector on the optical path of the X-ray.

6. The X-ray imaging apparatus according to claim 5, wherein
the diffraction grating comprises:
a first X-ray diffraction grating disposed at a position closer to the subject than the X-ray image detector; and
a second X-ray diffraction grating disposed at a position closer to the X-ray image detector than the first X-ray diffraction grating,
the first and the second X-ray diffraction gratings have a grating shape in which a membrane of a first grating thickness that has one thickness and a membrane of a second grating thickness that has a thickness different from the first grating thickness are alternately arranged, in the first X-ray diffraction grating, a difference between the first grating thickness and the second grating thickness is ¼ wavelength or ½ wavelength of the X-ray, and in the second X-ray diffraction grating, a difference between the first grating thickness and the second grating thickness is set to be 30% or more in terms of absorptivity of the X-ray.

7. The X-ray imaging apparatus according to claim 6, comprising a table that moves and rotates the second X-ray diffraction grating with respect to the first X-ray diffraction grating.

8. The X-ray imaging apparatus according to claim 1, wherein a single crystal plate is disposed between the subject and the X-ray image detector on the optical path of the X-ray, and the X-ray image detector is disposed on the optical path of the X-ray diffracted by the single crystal plate.

9. The X-ray imaging apparatus according to claim 8, comprising a table capable of adjusting an incident angle of an X-ray with respect to the single crystal plate with an accuracy of 1/100 arcseconds.

10. The X-ray imaging apparatus according to claim 1, wherein the X-ray image detector has energy resolution.

11. The X-ray imaging apparatus according to claim 10, wherein in the X-ray image detector, a threshold energy that defines a lower limit of detectable energy is set for each pixel constituting the X-ray image detector, and the X-ray image detector selectively detects an X-ray having energy greater than the threshold energy.

12. The X-ray imaging apparatus according to claim 11, wherein the X-ray image detector includes pixels with different threshold energies arranged in a checkered pattern.

13. An X-ray imaging method for obtaining an X-ray image of a subject with an X-ray, the method comprising:
    irradiating a subject with an X-ray;
    obtaining a plurality of first X-ray images by an X-ray image detection unit that detects an X-ray transmitted through the subject while changing an angle of the subject with respect to an optical path direction of the X-ray;
    moving the X-ray image detection unit when the angle has reached half rotation, and obtaining a plurality of second X-ray images while changing the angle again;
    repeatedly obtaining the first X-ray images and the second X-ray images; and
    calculating a sectional image of the subject from the repeatedly obtained first and second X-ray images.

14. The X-ray imaging method according to claim 13, wherein the X-ray image detection unit is moved in a plane perpendicular to an X-ray incident upon the subject, in two axial directions perpendicular to each other.

15. The X-ray imaging method according to claim 14, wherein the movement in the two axial directions is different for each of the two axial directions.

16. The X-ray imaging method according to claim 13, comprising:
    obtaining a spatial phase differential amount of the subject using a set of two diffraction gratings disposed between the subject and the X-ray image detection unit; and
    converting a phase shift of the X-ray which has occurred in the subject into an intensity of an X-ray based on the phase differential amount to detect the phase shift as an X-ray image.

17. The X-ray imaging method according to claim 16, wherein the set of two diffraction gratings includes a phase grating and an absorption grating.

18. The X-ray imaging method according to claim 17, comprising moving a distance corresponding to 1/m (m is a natural number of 3 or greater) of an interval between the diffraction gratings, which are the phase grating and the absorption grating, m−1 times, obtaining m X-ray images while changing, for each movement, a projection angle to the subject with respect to an optical path direction of the X-ray, and calculating a phase difference image at each projection angle from the obtained m X-ray images.

19. The X-ray imaging method according to claim 13, comprising:
    obtaining a plurality of X-ray diffraction images while changing a projection angle to the subject with respect to an optical path direction of the X-ray using a single crystal plate disposed between the subject and the X-ray image detection unit; and
    obtaining a spatial phase differential image of the subject at each projection angle from the plurality of X-ray diffraction images.

20. The X-ray imaging method according to claim 19, comprising:
    minutely rotating the single crystal plate under a condition close to a diffraction condition while changing an angle with respect to an optical path direction of the X-ray;
    obtaining, for each pixel constituting the X-ray image detection unit, an angle which maximizes an intensity of a diffracted X-ray, from a plurality of diffraction images obtained for each rotation; and
    detecting, from the angle, a refraction angle formed by the subject.

* * * * *